United States Patent [19]

Troxler et al.

[11] 4,067,873
[45] Jan. 10, 1978

[54] CERTAIN 1-AMINO-3-(1-ISOQUINOLINYL)OXY-2-PROPANOL DERIVATIVES

[75] Inventors: Franz Troxler; Erik Wiskott, both of Bottmingen, Switzerland

[73] Assignee: Sandoz Ltd., Basel, Switzerland

[21] Appl. No.: 668,597

[22] Filed: Mar. 19, 1976

[30] Foreign Application Priority Data

Mar. 26, 1975 Switzerland ........................ 3877/75

[51] Int. Cl.² .......................................... C07D 217/24
[52] U.S. Cl. ........................... 260/288 D; 260/286 R; 424/258
[58] Field of Search ..................................... 260/288 D

[56] References Cited

U.S. PATENT DOCUMENTS 3,340,266  9/1967  Howe et al. ..................... 260/288 R

FOREIGN PATENT DOCUMENTS 2,447,756  4/1975  Germany ......................... 260/288 D

*Primary Examiner*—R. Gallagher
*Attorney, Agent, or Firm*—Gerald D. Sharkin; Robert S. Honor

[57] ABSTRACT

This invention provides compounds of formula I,

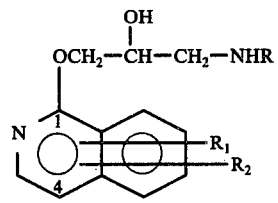

wherein
R is alkyl of 3 to 7 carbon atoms; cycloalkyl of 3 to 7 carbon atoms; cycloalkyl of 3 to 7 carbon atoms monosubstituted with alkyl of 1 to 4 carbon atoms; α-dialkylpropinyl of 5 to 9 carbon atoms; α-dialkylallyl of 5 to 9 carbon atoms; hydroxyalkyl of 2 to 7 carbon atoms, the hydroxy group thereof being separated by at least two carbon atoms from the nitrogen atom to which R is bound; phenethyl; phenethyl mono- or disubstituted in the phenyl residue independently when di-substituted with halogen of atomic number from 9 to 35, alkyl of 1 to 4 carbon atoms or unbranched alkoxy of 1 to 4 carbon atoms; or adamantyl; and
either $R_1$ is phenyl and $R_2$ is hydrogen;
or $R_1$ is alkyl of 1 to 4 carbon atoms or halogen of atomic number from 9 to 35 and $R_2$ is unbranched alkoxy of 1 to 4 carbon atoms or halogen of atomic number from 9 to 35, with the general proviso that the 8-position of the isoquinoline is unsubstituted and any halogen substituent which may be present in the 3- or 4- position is other than fluorine, useful for treating coronary diseases, arrhythmia, hyperlipoidemia and hyperglycemia.

4 Claims, No Drawings

CERTAIN 1-AMINO-3-(1-ISOQUINOLINYL)OXY-2-PROPANOL DERIVATIVES

The present invention relates to 1-(2-hydroxy-3-substituted-aminopropoxy)-isoquinolines.

More particularly this invention provides compounds of formula I,

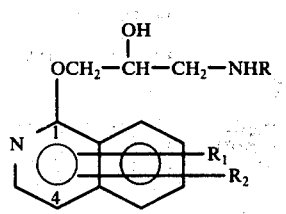

wherein
R is alkyl of 3 to 7 carbon atoms; cycloalkyl of 3 to 7 carbon atoms; cycloalkyl of 3 to 7 carbon atoms monosubstituted with alkyl of 1 to 4 carbon atoms; $\alpha$-dialkylpropinyl of 5 to 9 carbon atoms; $\alpha$-dialkylallyl of 5 to 9 carbon atoms; hydroxyalkyl of 2 to 7 carbon atoms, the hydroxy group thereof being separated by at least two carbon atoms from the nitrogen atom to which R is bound; phenethyl; phenethyl mono- or disubstituted in the phenyl residue independently when di-substituted with halogen of atomic number from 9 to 35, alkyl of 1 to 4 carbon atoms or unbranched alkoxy of 1 to 4 carbon atoms; or adamantyl; and
either $R_1$ is phenyl and $R_2$ is hydrogen;
or $R_1$ is alkyl of 1 to 4 carbon atoms or halogen of atomic number from 9 to 35 and $R_2$ is unbranched alkoxy of 1 to 4 carbon atoms or halogen of atomic number from 9 to 35, with the general proviso that the 8-position of the isoquinoline is unsubstituted and any halogen substituent which may be present in the 3- or 4- position is other than fluorine.

Preferably R and $R_1$ are alkyl.

When R is alkyl or hydroxyalkyl, the alkyl moiety is preferably branched, especially in an $\alpha$-position to the nitrogen atom to which R is bound. Specially preferred alkyl moieties are iso-propyl, tert.-butyl, 3-pentyl and tert.-pentyl, especially tert.-butyl.

An especially preferred hydroxyalkyl radical is 1,1-dimethyl-2-hydroxyethyl.

When R is cycloalkyl, this is preferably cyclopropyl, cyclopentyl or cyclohexyl.

When R is cycloalkyl substituted by alkyl, the alkyl substituent thereof is preferably methyl. Preferably the alkyl substituent is in the 1- position of the cycloalkyl group. Examples of interesting alkylcycloalkyl groups are 1-methylcyclopropyl and 1-methylcyclohexyl.

When R is the $\alpha$-dialkylpropinyl- or $\alpha$-dialkyl-allyl group defined above, the alkyl groups thereof are preferably identical. The alkyl groups especially signify methyl.

When R is a halogen substituted phenethyl group, halogen preferably is fluorine or chlorine, especially chlorine. Any alkyl or alkoxy substituents of the phenethyl radical preferably contain 1 or 2 carbon atoms, especially one carbon atom.

When $R_1$ and/or $R_2$ signify halogen, halogen is preferably fluorine or chlorine, especially chlorine.

When $R_1$ and/or $R_2$ signify alkyl or alkoxy of 1 to 4 carbon atoms, these radicals preferably contain 1 or 2 carbon atoms, especially 1 carbon atom.

$R_1$ is preferably in the 4-, 6- or 7- position, especially in the 4- position.

$R_2$ is preferably in the 7- position.

Any carbon-containing radical not particularly defined herein preferably has up to 5 carbon atoms.

The invention also provides a process for the production of compounds of formula I comprising reacting a compound of formula II,

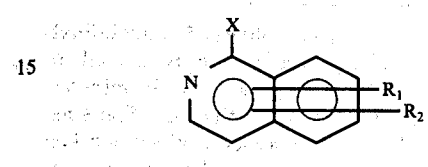

wherein
$R_1$ and $R_2$ are as defined above,
and X is an anionic leaving group,
with a compound of formula III,

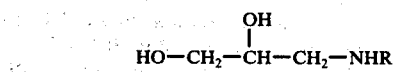

wherein R is as defined above, in free form or wherein the secondary hydroxy group and the terminal amine group are together protected in the form of an oxazolidine ring and hydrolysing any said ring to produce the corresponding compound of formula I.

The process may be effected in conventional manner for nucleophilic substitution. An inert organic solvent is preferably employed, for example a lower alcohol such as ethanol. A basic condensation agent is preferably used, for example an alkali metal alcoholate such as potassium tert.-butylate. The reaction temperature may vary between about 0° and 80° C, but room temperature is convenient.

X may, for example, be lower alkylthio such as methylthio, or bromine, preferably chlorine.

The hydrolysis may be effected under conventional conditions for the hydrolysis of oxazolidines, conveniently under acid conditions. The hydrolysis may suitably be effected at a temperature of from about 0° to about 80° C.

Such oxazolidines may conveniently be formed by the reaction of a compound of formula III with an aliphatic or aromatic aldehyde or ketone, for example propionaldehyde, benzaldehyde and acetone.

The resulting compounds of formula I may be isolated from the reaction mixture and purified in known manner.

Free base forms of the compounds of formula I may be converted into acid addition salt forms and vice versa. Suitable acids for salt formation include maleic acid, formic acid and naphthalene-1,5-disulphonic acid.

In the compounds of formula I, the carbon atom of the side chain bearing the hydroxy group is asymmetrically substituted and accordingly the compounds of formula I can exist in enantiomeric forms.

The enantiomeric forms of the compounds of formula I can be obtained by known methods, for example, by effecting the process of the invention with an appropriate enantiomer of compound III, starting from the appropriate glyceraldehyde.

Insofar as the production of starting materials is not described, these are known or may be produced in accordance with known processes, or in a manner analogous to the process described herein or to known processes.

In the following non-limitative Examples all temperatures are indicated in degrees Celsius and are uncorrected.

EXAMPLE 1

1-(2-Hydroxy-3-tert.-butylaminopropoxy)-7-chloro-4-methylisoquinoline 1 g of 1-(3-tert.-Butyl-2-phenyl-5-oxazolidinyl-methoxy)-7-chloro-4-methylisoquinoline is heated to 80° in 10 ml of 1N hydrochloric acid for 10 minutes. The reaction mixture is extracted with ether. The ethereal phase is discarded and the aqueous phase worked up to yield the title compound in free base form. M.p. 116°–117°.

The 1-(3-tert.-butyl-2-phenyl-5-oxazolidinyl-methoxy)-7-chloro-4-methylisoquinoline, required as starting material, is obtained as follows:

a. Hydrogenation of glycerinaldehyde and tert.-butylamine with 10% palladium on charcoal yields 1-tert.-butylamino-2,3-dihydroxypropane. M.p. 80°–82°.

b. The 3-tert.-butyl-5-hydroxymethyl-2-phenyloxazolidine (b.p. 127° at 0.5 mm), required for the reaction, is obtained by boiling 1-tert.-butylamino-2,3-dihydroxypropane with an excess of benzaldehyde in benzene on a water separator.

c. 0.74 g of Potassium is dissolved in 15 ml of absolute tert.-butanol and 4.0 g of 1,7-dichloro-4-methylisoquinoline [m.p. 90°–92°: preparable in manner analogous to that described in Helv. Chim. Acta 52 (1969) 1755–1762 for the preparation of 1,7-dichloro-3-methylisoquinoline] and 4.4 g of 3-tert.-butyl-5-hydroxymethyl-2-phenyloxazolidine are added. The solution is heated to 50° for 1 hour, whereupon it is evaporated to dryness. The product is digested in water, extracted with ether, the ether phase dried and the ether distilled off. 1-(3-tert.-Butyl-2-phenyl-5-oxazolidinyl-methoxy)-7-chloro-4-methylisoquinoline is obtained as an oil.

EXAMPLE 2

1-(2-Hydroxy-3-tert.-butylaminopropoxy)-7-chloro-4-methylisoquinoline 0.74 g of Potassium is dissolved in 40 ml of tert.-butylalcohol and 3.0 g of 1-tert.butylamino-2,3-dihydroxypropane and subsequently 4 g of 1,7-dichloro-4-methylisoquinoline are added. After stirring for one day, heating up to 50° is effected for a further day. The reaction solution is concentrated by evaporation under vacuum. The residue is taken up with 1N hydrochloric acid and ether, the aqueous phase neutralised with 2N caustic soda solution and extracted with methylene chloride. After drying over magnesium sulphate and concentration by evaporation the title compound is obtained in free base form. M.p. 116°–117°.

In manner analogous to Examples 1 and 2, but employing appropriate starting materials in approximately equivalent amounts, the following compounds can be obtained.

| Ex. | R | $R_1$ | $R_2$ | M.P. |
|---|---|---|---|---|
| 3 | $C(CH_3)_3$ | 7-phenyl | H | hydrogen |
| 4 | $C(CH_3)_3$ | 6-Cl | 7-Cl | maleate 176–177° naphthalene-1,5-disulphonate 241–243° |
| 5 | $C(CH_3)_3$ | 4-$CH_3$ | 7-$OCH_3$ | hydrogen fumarate 162–165° |
| 6 | ▷— | 3-$C_2H_5$ | 6-F— | |
| 7 | $C_2H_5$—⬡— | 4-$C_2H_5$— | 7-$CH_3O$— | |
| 8 | —$C(CH_3)_2$—C≡CH | 5-$C_3H_7$— | 6-$CH_3O$— | |
| 9 | —$C(CH_3)_2C$=C=$CH_2$ | 5-$C_4H_9$ | 7-F— | |
| 10 | $C_4H_8(OH)$—$C(CH_3)_2$— | 4-$CH_3$ | 7-$C_2H_5O$— | |
| 11 | ⬡—$CH_2CH_2$— | 4-Br | 5-F— | |
| 12 | CL—⬡—$CH_2CH_2$— | 3-Cl | 6-Br | |
| 13 | $CH_3O$—⬡—$CH_2CH_2$— | 3-$CH_3$— | 5-Br | |
| 14 | $CH_3$—⬡—$CH_2CH_2$— | 3-Br | 6-$C_4H_9O$— | |
| 15 | F—⬡($C_2H_5$)—$CH_2CH_2$— | 3-$C_3H_8$ | 7-$C_3H_7O$— | |
| 16 | adamantyl | 3-$C_2H_5$ | 7-Br | |

The compounds of formula I are useful because they possess pharmacological activity in animals. In particular, the compounds are useful as β-adrenoceptor blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, as indicated in standard tests, e.g. by an inhibition of the positive inotropic adrenaline effect in the spontaneously beating guinea pig atrium at a bath concentration of from 0.005 to 5 mg/liter, in accordance with the method of K. Sammeli, Helv. Physiol. Acta. 25 CR 215–221 (1967).

For the above-mentioned use, the dosage administered will, of course, vary depending on the compound employed, mode of administration and treatment desired. However, in general, satisfactory results are obtained with a daily dosage of from about 0.005 to 10 mg/kg animal body weight, conviently given in divided doses 2 to 4 times a day or in sustained release form. For the larger mammal, the total daily dosage is in the range of from about 1 to 500 mg, and dosage forms suitable for oral administration comprise from about 0.25 to 250 mg of the compound, admixed with a solid or liquid pharmaceutical carrier or diluent. An example of a daily dosage is from about 0.01 to 1 mg/kg, e.g. from about 1 to 100 mg, conveniently given in divided dosages 2 to 4 times a day in dosage forms comprising from about 0.25 to about 50 mg of the compound or in sustained release form.

The compounds are furthermore particularly useful as inhibitors of hyperlipoidemia induced by emotional stress and also as agents for the treatment or prophylaxis of myocardism as indicated in standard tests for showing inhibition of increased free fatty acid concentration due to mobilisation, and lipolysis, in blood induced by emotional stress, for example, by an inhibition of glycerol release stimulated by isoproterenol (i) in vitro, e.g. at a concentration of about 0.1 to about 10 mg/l solution of the compounds in fat cells of the epididymal fat tissue of rats, the cells having been isolated in accordance with the method of M. Rodbell [J. Biol. Chem. 239, 375–80 (1964)], and (ii) in vivo, e.g. in rats on s.c. administration of from about 0.01 to about 1 mg/kg animal body weight of the compounds.

The compounds are furthermore useful as inhibitors of hyperglycemia induced by emotional stress and therefore as suppressants of appetite induced by emotional stress, as indicated in standard tests, e.g. by an inhibition of glucose release stimulated by isoproterenol in rats in vivo on s.c. administration of from about 0.01 to about 1 mg/kg of animal body weight of the compounds.

For the above-mentioned emotional stress uses for stress conditions the dosages will, of course, vary depending on the compound employed, mode of administration and treatment desired. However, in general, satisfactory results are obtained with a daily dosage of from about 0.01 to about 10 mg/kg animal body weight, conveniently given in divided doses 2 to 4 times a day or in sustained release form. For the larger mammal, the total daily dosage is in the range from about 1 to about 200 mg, e.g. up to 100 mg, and dosage forms suitable for oral administration comprise from about 0.25 to about 100 mg, e.g. up to 50 mg, of the compounds admixed with a solid or liquid pharmaceutical carrier or diluent.

The compounds are furthermore particularly useful as anti-arrhythmic agents, e.g. for the treatment of heart rhythm disorders, as indicated in standard tests, for example by a protection against cardiac arrythmia induced by chloroform in mice on i.p. administration of from 10 to 50 mg/kg animal body weight of the compounds in accordance with the principles of J. W. Lawson [J. Pharmacol. Exp. Therap. (1968) 160 22–31].

For this use the dosage will, of course, vary depending on the compound employed, mode of administration and treatment desired. However, in general, satisfactory results are obtained with a daily dosage of from about 0.1 to about 50 mg/kg animal body weight, conveniently given in divided doses 2 to 4 times a day or in sustained release form. For the larger mammal, the total daily dosage is in the range from about 7 to about 700 mg, and dosage forms suitable for oral administration comprise from about 2 to about 350 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixers, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

In one group of compounds, R is alkyl of 3 to 7 carbon atoms; cycloalkyl of 3 to 7 carbon atoms; cycloalkyl of 3 to 7 carbon atoms mono-substituted with alkyl of 1 to 4 carbon atoms; α-dialkylpropinyl of 5 to 9 carbon atoms; α-dialkylallyl of 5 to 9 carbon atoms; hydroxyalkyl of 2 to 7 carbon atoms, the hydroxy group thereof being separated by at least two carbon atoms from the nitrogen atom to which R is bound; or adamantyl.

In a second group of compounds, R is phenethyl; phenethyl mono- or disubstituted in the phenyl residue independently when disubstituting with halogen of atomic number from 9 to 35, alkyl of 1 to 4 carbon atoms or unbranched alkoxy of 1 to 4 carbon atoms.

In a third group of compounds $R_1$ is phenyl and $R_2$ is hydrogen.

In a fourth group of compounds, $R_1$ is alkyl of 1 to 4 carbon atoms or halogen of atomic number from 9 to 35 and $R_2$ is unbranched alkoxy of 1 to 4 carbon atoms or halogen of atomic number from 9 to 35.

What is claimed is:

1. A compound of the formula

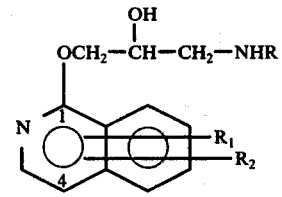

wherein
R is alkyl of 3 to 7 carbon atoms; cycloalkyl of 3 to 7 carbon atoms; cycloalkyl of 3 to 7 carbon atoms monosubstituted with alkyl of 1 to 4 carbon atoms; α-dialkylpropinyl of 5 to 9 carbon atoms; α-dialkylallyl of 5 to 9 carbon atoms; hydroxyalkyl of 2 to 7 carbon atoms; the hydroxy group thereof being separated by at least two carbon atoms from the nitrogen atom to which R is bound; phenethyl; phenethyl mono- or disubstituted in the phenyl residue independently when di-substituted with fluoro, chloro or bromo, alkyl of 1 to 4 carbon atoms or unbranched alkoxy of 1 to 4 carbon atoms; or adamantyl; and
either $R_1$ is phenyl and $R_2$ is hydrogen;
or $R_1$ is alkyl of 1 to 4 carbon atoms or fluoro, chloro or bromo and $R_2$ is unbranched alkoxy of 1 to 4 carbon atoms or fluoro, chloro or bromo, with the general proviso that the 8-position of the isoquinoline is unsubstituted and any halogen substitutent which may be present in the 3- or 4-position is other than fluorine,
or a pharmaceutically acceptable acid addition salt form thereof, or an active enantiomer or racemic mixture thereof.

2. A compound of claim 1 in (S)-enantiomeric form.

3. A compound of claim 1 in (R)-enantiomeric form.

4. A compound of claim 1 in the form of a racemic mixture.